(12) United States Patent
Park et al.

(10) Patent No.: US 7,994,310 B2
(45) Date of Patent: Aug. 9, 2011

(54) PROCESS FOR PREPARING 2'-DEOXY-2', 2'-DIFLUOROCYTIDINE

(75) Inventors: Su-Jin Park, Seongnam-si (KR); Chun-Rim Oh, Seoul (KR); Young-Deuck Kim, Suwon-si (KR)

(73) Assignee: Dongwoo Syntech Co., Ltd., Chungcheonbuk-Do (KR)

( * ) Notice: Subject to any disclaimer, the term of this patent is extended or adjusted under 35 U.S.C. 154(b) by 122 days.

(21) Appl. No.: 12/532,331

(22) PCT Filed: Mar. 20, 2008

(86) PCT No.: PCT/KR2008/001566
§ 371 (c)(1),
(2), (4) Date: Sep. 21, 2009

(87) PCT Pub. No.: WO2008/117955
PCT Pub. Date: Oct. 2, 2008

(65) Prior Publication Data
US 2010/0069625 A1   Mar. 18, 2010

(30) Foreign Application Priority Data

Mar. 23, 2007 (KR) .................. 10-2007-0028526
Dec. 12, 2007 (KR) .................. 10-2007-0128809

(51) Int. Cl.
*C07H 19/073* (2006.01)
(52) U.S. Cl. .................................. 536/27.11; 536/28.5
(58) Field of Classification Search ........................ None
See application file for complete search history.

(56) References Cited

U.S. PATENT DOCUMENTS

| 4,526,988 A | 7/1985 | Hertel |
| 4,965,374 A | 10/1990 | Chou et al. |
| 5,223,608 A | 6/1993 | Chou et al. |
| 5,371,210 A | 12/1994 | Chou |
| 5,401,838 A | 3/1995 | Chou |
| 5,401,861 A | 3/1995 | Chou |
| 5,426,183 A | 6/1995 | Kjell |
| 5,434,254 A | 7/1995 | Chou et al. |
| 5,453,499 A | 9/1995 | Chou et al. |
| 5,594,124 A | 1/1997 | Chou |
| 5,606,048 A | 2/1997 | Chou et al. |
| 5,744,597 A | 4/1998 | Chou et al. |

FOREIGN PATENT DOCUMENTS

| EP | 0577304 B1 | 3/1997 |
| KR | 10-2006-0008056 | 1/2006 |
| KR | 10-2006-0047970 | 5/2006 |
| WO | 2005/095430 A1 | 10/2005 |
| WO | 2006/009353 A1 | 1/2006 |
| WO | 2006/095359 A1 | 9/2006 |

*Primary Examiner* — Lawrence E Crane
(74) *Attorney, Agent, or Firm* — Lucas & Mercanti, LLP

(57) ABSTRACT

Disclosed is a method for preparing 2'-deoxy-2',2'-difluorocytidine of Formula I comprising, preparing an optically pure 3R-hydroxypropane amide compound of Formula VIII from an optical ester compound of Formula IX using an optically active chiral amine, preparing an optically pure D-erythro-2, 2-difluoro-2-deoxy-1-oxoribose compound of Formula V from the compound of Formula VIII, glycosylating the compound of Formula V with a nucleobase to prepare the 2'-deoxy-2',2'-difluorocytidine of Formula I as a β-nucleoside. With the present invention, it is possible to prepare an optically pure compound of Formula I in a high purity and a high yield. In the Formulae, $R_1$ and $R_2$ are protecting groups and are each independently benzoyl, 4-methylbenzoyl, 3-methylbenzoyl, 4-cyanobenzoyl, 3-cyanobenzoyl, 4-propylbenzoyl, 2-ethoxybenzoyl, 4-t-butylbenzoyl, 1-naphthoyl or 2-naphthoyl, $R_3$, $R_4$ and $R_7$ are each independently $C_1$-$C_3$ alkyl, $R_5$ is methyl or ethyl, $R_6$ is hydrogen, methyl or methoxy.

5 Claims, No Drawings

PROCESS FOR PREPARING 2'-DEOXY-2', 2'-DIFLUOROCYTIDINE

CROSS-REFERENCE TO RELATED APPLICATIONS

This application is a 371 of PCT/KR2008/001566 filed on Mar. 20, 2008, which claims the benefit of Korean Patent Application Nos. 10-2007-0028526 filed on Mar. 23, 2007 and 10-2007-0128809 filed on Dec. 12, 2007, the contents of each of which are incorporated herein by reference.

TECHNICAL FIELD

The present invention relates to a process for preparing of 2'-deoxy-2',2'-difluorocytidine represented by Formula I below:

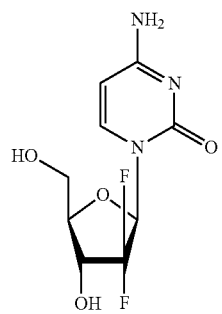

(I)

The compound of Formula I above, also known as "gemcitabine", is a nucleoside that has structurally a ribofuranose backbone and is a 2'-deoxy-2',2'-difluoronucleoside compound having a cytosine nucleobase stereochemically oriented upward in the β-direction at C-1 of the ribofuranose backbone. Gemcitabine is widely used as an antitumor agent to treat various carcinomas including non-small cell lung cancer (NSCLC), pancreatic cancer, bladder cancer, breast cancer and ovarian cancer.

The considerably important key to prepare gemcitabine is to develop a method for efficiently synthesizing D-erythro-1-oxoribose represented by the following Formula V having a D-erythro structure in which a hydroxyl group on the 3-carbon or a protective group-introduced hydroxyl group thereon is oriented downward.

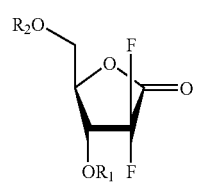

(V)

wherein $R_1$ and $R_2$ are protective groups and are each independently benzoyl, 4-methylbenzoyl, 3-methylbenzoyl, 4-cyanobenzoyl, 3-cyanobenzoyl, 4-propylbenzoyl, 2-ethoxybenzoyl, 4-t-butylbenzoyl, 1-naphthoyl or 2-naphthoyl.

BACKGROUND ART

There are several conventional methods for preparing D-erythro 1-oxoriboses. For example, U.S. Pat. No. 4,526,988 discloses a process for separating alkyl 2,2-difluoro-3-hydroxy-3-(2,2-dialkyldioxolan-4-yl)propionate consisting of a 3:1 mixture of 3R-hydroxy enantiomers and 3S-hydroxy enantiomers represented by the following formulae 1 and 2 by column chromatography.

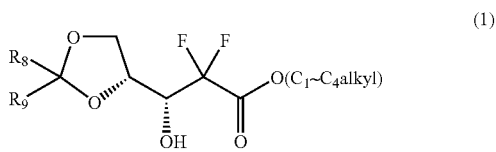

(1)

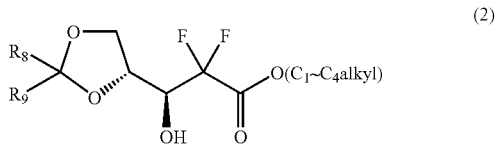

(2)

wherein $R_8$ and $R_9$ are each independently $C_1$-$C_3$ alkyl.

The 3R-hydroxy enantiomer of Formula I is reacted with a strong acid to hydrolyze the dioxolane group and proceed the lactonization reaction, to obtain 2,2-difluoro-2-deoxy-D-erythro-1-oxoribose (3) having a erythro structure in which the 3-hydroxyl group is oriented downward, as depicted in Reaction Scheme 1 below.

[Reaction Scheme 1]

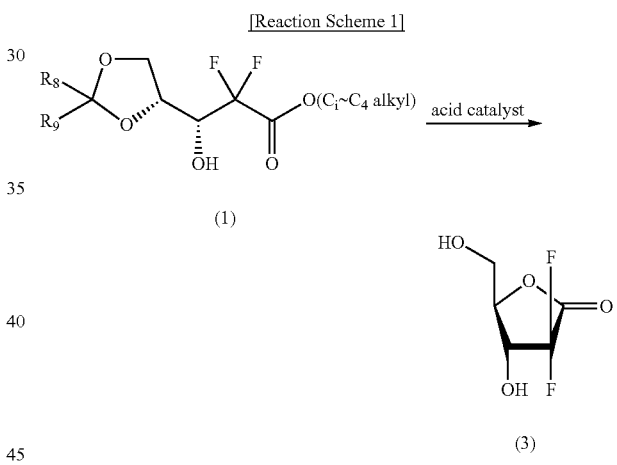

Column chromatography, used in the aforementioned method, is not suitable for mass-production due to limitations on column sizes and the amounts of materials loaded. In particular, column chromatography requires the use of expensive silica gel as column filler and an excess amount of developing solvent, thus disadvantageously involving high costs.

U.S. Pat. Nos. 4,965,374, 5,223,608 and 5,434,254 disclose a method for separating a desired erythro enantiomer (7) as a precipitate from a mixture of erythro and threo lactones, as depicted in Reaction Scheme 2 below, comprising hydrolyzing 3-benzoyloxypropionate ester (4) (as a 3:1 enantiomeric mixture of 3R- and 3S-enantiomers) with an acid, subjecting the compound to azeotropic distillation with water in order to minimize a reverse reaction toward the precursors to provide a lactone ring (5) as a mixture of erythro and threo lactones, protecting the 5-hydroxyl group with a benzoyl group to provide a 3,5-dibenzoyloxy compound (6), and cooling the compound to a low temperature of −5° C. to 10° C. in dichloromethane to separate a desired erythro enantiomer (7) as a precipitate from the mixture of erythro and threo lactones.

[Reaction Scheme 2]

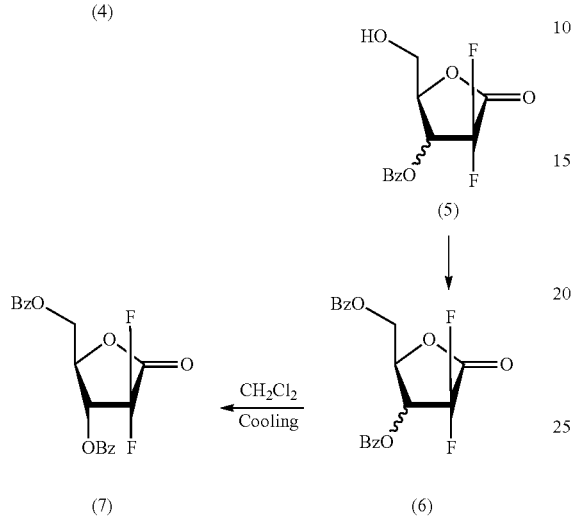

wherein Bz indicates a benzoyl group.

This method is characterized in that the 3-benzoyl oxypropionate ester (4), a mixture of 3R- and 3S-enantiomers, is used for the lactone ring reaction without being separated. In particular, in accordance with the method, 3,5-dibenzyl-1-oxoribose (6) (the mixture of erythro and threo) is dissolved in water and the mixture is cooled to a low temperature, thereby readily selectively separating and obtaining the erythro 3,5-dibenzoyl enantiomer (7). However, this method suffers from several disadvantages including use of highly corrosive, toxic, and expensive trifluoroacetic acid in an excessive amount of 3 equivalents or more for the lactone ring reaction, and being uneconomical due to considerably low overall reaction yield (i.e., about 25%) to obtain the 3,5-dibenzoyl enantiomer (7) from the 3-benzoyl oxypropionate ester (4) as a starting material.

In addition, Korean Patent Application No. 10-2004-0057711 suggests a method for preparing a D-erythro enantiomer (11), as depicted in the following Reaction Scheme 3, comprising introducing a stereochemically large protecting group into the hydroxyl group of the compound (8) to obtain a compound (9), treating the compound (9) with a base to obtain a 3R-enantiomer (10) as an optically pure salt, and subjecting the 3R-enantiomer (10) to lactonization under strong acidic conditions to obtain the target D-erythro enantiomer (11).

[Reaction Scheme 3]

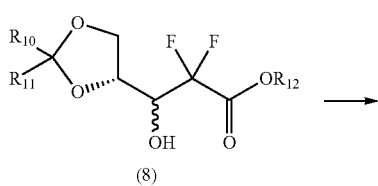

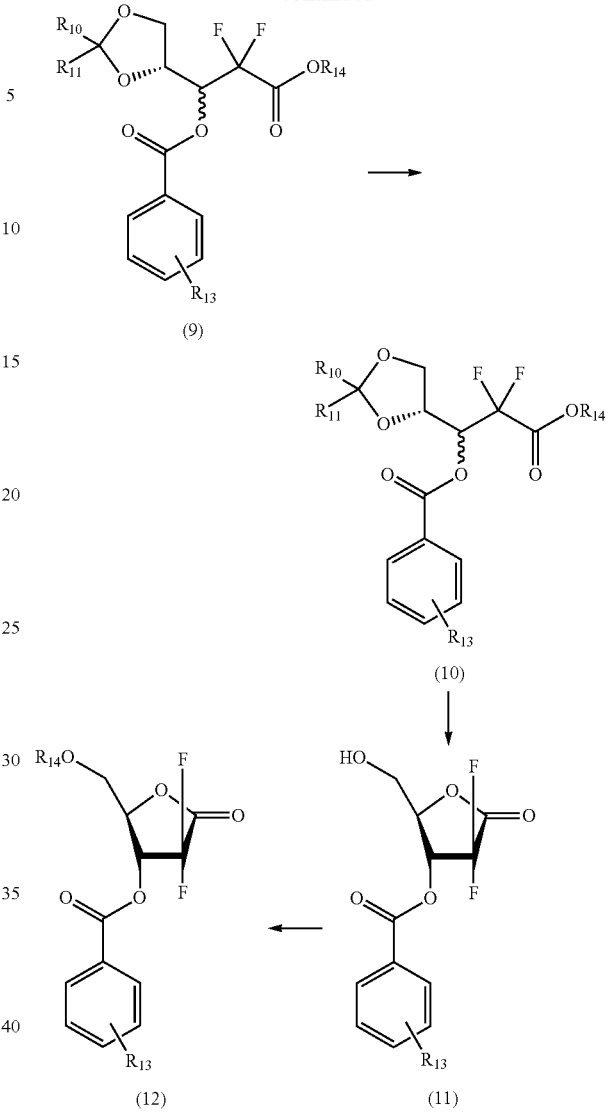

wherein $R_{10}$, $R_{11}$ and $R_{12}$ are $C_1$-$C_3$ alkyl, $R_{13}$ is phenyl or substituted phenyl, and M is $NH_3$, Na or K.

This method suffers from disadvantages in that biphenyl-4-carbonyl chloride, the compound used as the protecting group, is costly, as compared to benzoyl and naphthoyl compounds generally used as protecting groups, and 3R-carboxylic acid ester enantiomers can be separated, but 3S-carboxylic acid ester enantiomers cannot be separated.

As apparent from the foregoing, the conventionally known methods have the following disadvantages. The methods are not suitable for mass-production since 3R-hydroxy enantiomers as precursors are separated by the use of column chromatography or introduction of expensive protecting groups in order to synthesize an erythro 1-oxoribose compound by hydrolyzing the 3R-hydroxyl group enantiomers. Selectively obtaining 3R- and 3S-hydroxy compounds using the methods is difficult. Furthermore, although the lactonization reaction is completed in the form of the mixture of 3R- and 3S-hydroxyl compounds, only the erythro enantiomers are selectively separated from an enantiomeric mixture of erythro and threo 1-oxoribose compounds, thus involving a considerably low yield and low economical efficiency.

The 2'-deoxy-2',2'-difluorocytidine of Formula I is prepared in accordance with a conventional method, as depicted in the following Reaction Scheme 4. More specifically, the 2'-deoxy-2',2'-difluorocytidine can be prepared by converting a keto moeity in the lactone of the lactone compound (12) into an alcohol to obtain a lactol compound (13), converting the lactol compound into a ribofuranose intermediate (14), into which a highly reactive leaving group is introduced, due to the difficulty of directly glycosylating the 1-hydroxyl group of the lactol compound with a nucleobase, reacting the activated ribofuranose intermediate with a nucleobase to obtain a nucleoside which is subsequently deprotected.

[Reaction Scheme 4]

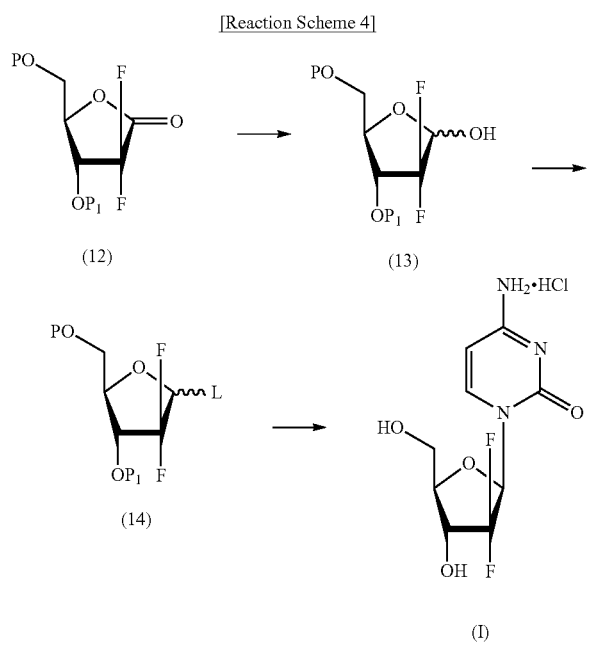

wherein P and $P_1$ are each independently a hydroxyl protecting group, and L is a leaving group.

P and $P_1$, the hydroxyl protecting groups of the compound (12), are benzoyl groups in almost all conventional methods, other than that disclosed in Korean Patent Application No. 10-2004-0057711. Korean Patent Application No. 10-2004-0057711 also has a limitation of restricting the 3-protecting group to 4-phenyl-benzoyl.

It is known that sulfonyloxy and halo groups may be used as the leaving groups, and in particular, the most preferred of the sulfonyloxy groups is α-methanesulfonyloxy ribofuranose.

The glycosylation of Reaction Scheme 5 is carried out in accordance with an SN2 reaction mechanism in which a nucleobase attacks the leaving group on the 1-carbon of D-erythro-ribofuranose and then undergoes substitution. To prepare nucleoside, in which the cytosine base of gemcitabine is oriented in the β-position, in high yield, it is important to obtain an α-anomer having a leaving group in the α-position in high yield.

Generally, in connection with the reaction, in which the nucleobase attacks the leaving group on the 1-carbon of D-erythro-ribofuranose and is then substituted, the leaving group released after the reaction attacks the C-1 position, while competing with the nucleobase, to induce anomerization at the C-1 position, thus shifting a ratio of α-anomers to β-anomers from the initial stage of the reaction. That is, although only α-anomers are used for glycosylation, β-anomers increase in amount with the passage of time. As a result, the reaction proceeds non-steroselectively, thus resulting in production of α-nucleosides as impurities as well as desired β-nucleosides oriented at the β-position.

In the case where the leaving group is sulfonyloxy, such anomerization is decreased. Accordingly, when pure α-sulfonyloxy anomers, for example, α-methanesulfonyloxy compounds, are used, an excess of the desired β-nucleosides can be obtained.

On the other hand, in the case where the leaving group is haloRPS, although only pure α-halo anomers are used for glycosylation, the level of anomerization by halides released after the reaction is relatively high, and β-halo anomers are thus gradually increased as the reaction proceeds. In particular, the β-halo anomers have a higher glycosylation rate than that of α-halo anomers, and the halo leaving group has a lower reactivity than that of the sulfonyloxy leaving group, thus requiring longer reaction time and higher reaction temperature, and therefore showing lower stereoselectivity, allowing the α-nucleosides to increase as the reaction proceeds.

Accordingly, in the preparation of 2'-deoxy-2',2'-difluoro nucleoside employing the glycosylation reaction, the method using 1-halo-ribofuranose inevitably entails limited stereoselectivity. For this reason, the method for preparing the nucleosides using the α-methanesulfonyloxy ribofuranose is known to be the most excellent of conventionally developed glycosylation methods.

A more-detailed illustration of this method will be given. First, the methods for glycosylating α-sulfonyloxy ribofuranose with nucleobases are disclosed in U.S. Pat. Nos. 5,371,210, 5,401,838, 5,426,183, 5,594,124, and 5,606,048 and European Patent No. 577,303. As depicted in Reaction Scheme 5 below, these methods involve stereoselective glycosylation comprising reacting a 1-sulfonyloxy ribofuranose derivative (15) containing a sufficient amount of anomer with a nucleobase to produce a β-nucleoside (16) in a high ratio.

[Reaction Scheme 5]

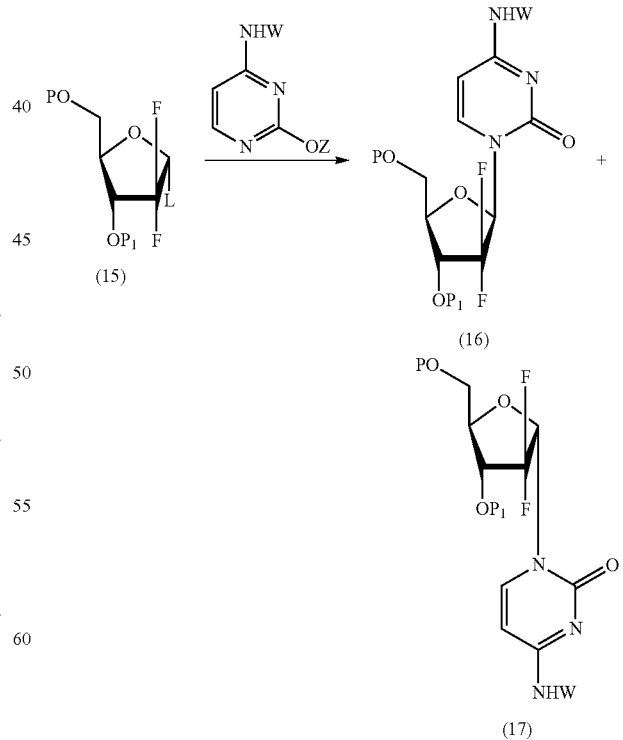

wherein P and $P_1$ are hydroxyl protecting groups, W is an amino protecting group or hydrogen, L is a leaving group, including sulfonyloxy substituted with nitrile, halo, carboalkoxy or nitro, substituted sulfonyloxy, or substituted arylsulfonyloxy.

In accordance with this method, about 5 to 7-times as many β-nucleosides (16), in which nucleobases are mostly oriented in the β-position, are obtained as α-nucleosides (17) due to good reactivity and a low level of anomerization of the 1-sulfonyloxy leaving group. As a result, gemcitabine can be obtained in yields as high as 30 to 75%.

Meanwhile, U.S. Pat. Nos. 4,526,988 and 5,453,499 and Korean Patent Application No. 10-2005-0041278 disclose 1-α-halo-ribofuranose derivatives into which halo leaving groups are introduced.

[Reaction Scheme 6]

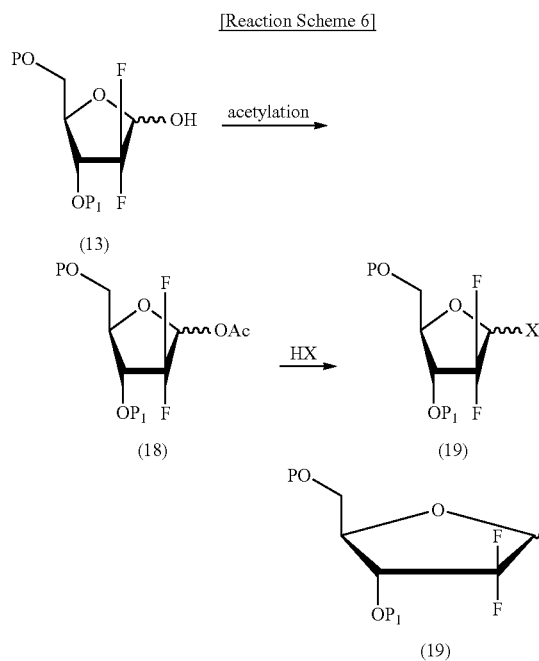

wherein P and $P_1$ are hydroxyl protecting groups, Ac is an acetyl group, and X is bromo or chloro.

U.S. Pat. No. 4,526,988 discloses a method for preparing a 1-halo anomer (19), as depicted in Reaction Scheme 6, comprising reacting the 1-hydroxyl group of a lactol compound (13) with acetic anhydride or another acetyl-based source in the presence of 1 equivalent or more of an acid scavenger to prepare a 1-acetate derivative (18) and adding a hydrobromide or hydrochloride gas to the reaction mixture at a low temperature of about −50 to 0° C. to obtain a 1-halo anomer (19). However, this method has a disadvantage of yielding the α-halo anomer in low yield due to low stereoselectivity.

[Reaction Scheme 7]

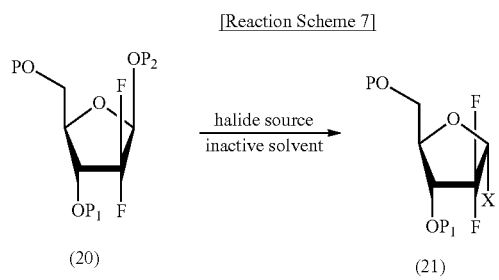

wherein P and $P_1$ are hydroxyl protecting groups such as benzoyl, $P_2$ is sulfonyl and X is halide.

U.S. Pat. No. 5,453,499 discloses a method for preparing a high ratio of α-halo anomers (21) to β-halo anomers of 9:1 to 10:1 by reacting a β-sulfonyloxy compound (20) with a halide source in an inactive solvent, as depicted in Reaction Scheme 7.

The β-sulfonyloxy compound (20) as a starting material is prepared from the corresponding 1-hydroxyl compound disclosed in U.S. Pat. No. 5,401,861. In the preparation of the β-sulfonyloxy compound (20), α-sulfonyloxy anomers and β-sulfonyloxy anomers are prepared in a ratio of 1:4. However, when taking into consideration the process of separating the β-sulfonyloxy anomers from the mixture of α- and β-anomers, although α-halo anomers are obtained in a high ratio of 9:1 to 10:1 (α-anomer:β-anomer) in Reaction Scheme 7 above, a stereoselectivity ratio of the final α-halo anomers (21) to β-halo anomers obtained from the 1-hydroxy compound is at most 3:1. In addition, since the α-halo anomers (21), into which benzoyl groups as 3- and 5-hydroxyl protecting groups are introduced, are yielded in an oil phase, they disadvantageously require the use of column chromatography which is unsuitable for mass-production due to low separation efficiency and low economical efficiency. In particular, the oil phase thus obtained is generally difficult to handle or store, similar to solids.

[Reaction Scheme 8]

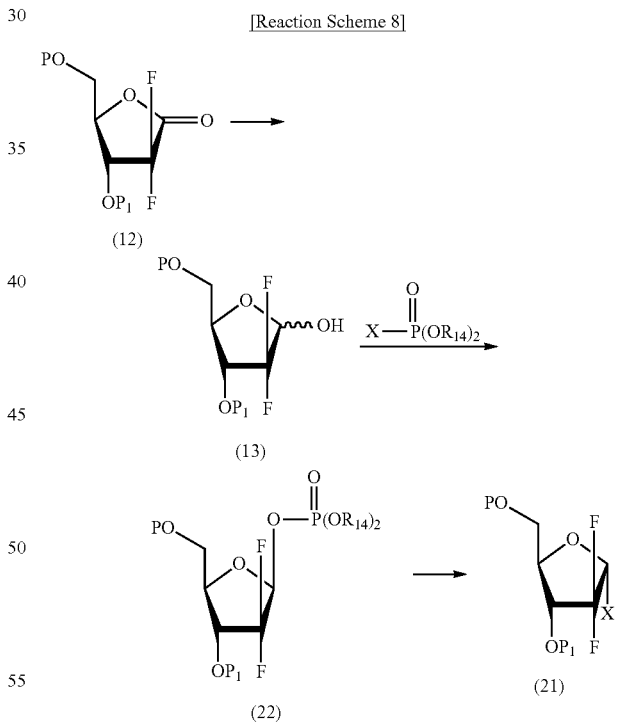

As depicted in Reaction Scheme 8. Korean Patent Application No. 10-2005-0041278 discloses a method for preparing α-halo anomers (21), comprising reacting a lactol compound (13) with a phosphenyl halide compound in the presence of a base to prepare a 1-phosphenyloxy furanose derivative (22), reacting the compound (22) with a halide source and recrystallizing the resulting product.

However, this method suffers from disadvantages of complicated reaction procedure, and the difficulty of yielding the compound with a high purity due to the difficulty of removing phosphenyl acid obtained as by-products.

In addition, there are several conventional glycosylation methods using 1-haloribofuranose. For example, U.S. Pat. No. 5,744,597 and European Patent No. 577,304 disclose a stereoselective anion glycosylation process, as depicted in Reaction Scheme 9 below, comprising reacting an α-halo anomer-rich ribofuranose derivative (15) with an anionic nucleobase to prepare a β-nucleoside (16) having the nucleobase introduced at the β-position.

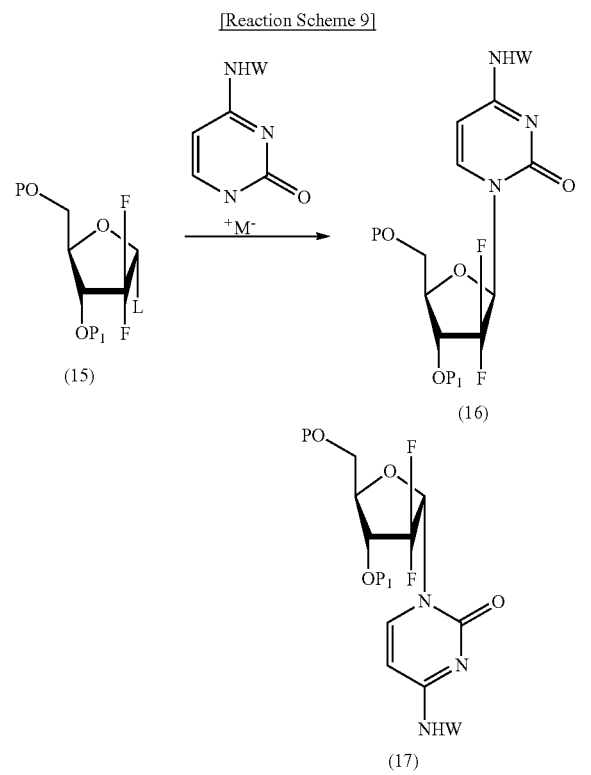

wherein P and $P_1$ are hydroxyl protecting groups, W is an amino protecting group, $M^+$ is an anion, and L is iodine or sulfonyloxy.

In accordance with this method, the nucleobase is reacted with a strong base such as potassium t-butoxide or sodium hydride to prepare an anionic nucleobase, and the anionic nucleobase is glycosylated with an α-halo anomer-rich ribofuranose derivative (15) to obtain an α-nucleoside (17) as well as a β-nucleoside (16). This method has several disadvantages of the necessity of an additional troublesome process to prepare the anionic nucleobase, in particular, of yielding an equivalent amount of the desired β-nucleosides and α-nucleosides due to nonstereoselective glycosylation, as mentioned above, and inefficiency and low economical efficiency due to a considerably low separation yield.

As such, in the case where 1-haloribofuranose containing halide as the leaving group is used for glycosylation, although pure α-anomers oriented at the α-position only are used, the glycosylation reaction proceeds nonstereoselectively, unlike the case where α-sulfonate leaving groups are used, thus showing inferior results, namely that the desired α-nucleoside is yielded in a considerably low yield.

In addition, obtaining different P and $P_1$ hydroxyl protecting groups introduced at the 3- and 5-positions, shown in Reaction Scheme 9 above, is difficult, necessitating that P and $P_1$ be identical.

DISCLOSURE

Technical Problem

Therefore, one object of the present invention is to provide a method for preparing 2'-deoxy-2',2'-difluorocytidine of Formula I, which comprises preparing an optically pure 3R-hydroxypropane amide compound represented by the following Formula VIII from an optical ester compound represented by Formula IX using optically pure amine; preparing an optically pure D-erythro-2,2-difluoro-2-deoxy-1-oxoribose compound represented by Formula V, into which various 3- and 5-hydroxyl protecting groups are introduced, from the optically pure 3R-hydroxypropane amide compound of Formula VIII; and preparing the 2'-deoxy-2',2'-difluorocytidine of Formula I from the compound of Formula V.

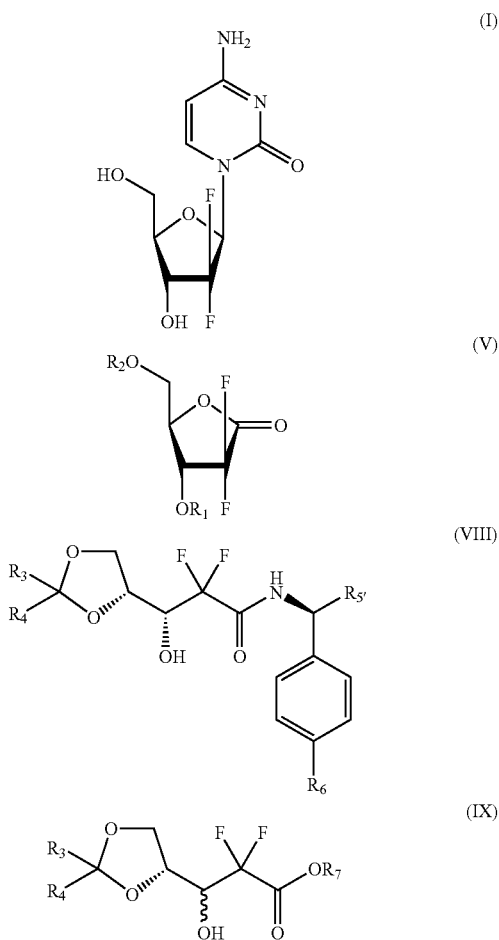

wherein $R_1$ and $R_2$ are a protecting group, and when $R_1$ is 1-naphthoyl or 2-naphthoyl, $R_2$ is benzoyl, 4-methylbenzoyl, 3-methylbenzoyl, 4-cyanobenzoyl, 3-cyanobenzoyl, 4-propylbenzoyl, 2-ethoxybenzoyl or 4-t-butylbenzoyl, and when $R_2$ is 1-naphthoyl or 2-naphthoyl, $R_1$ is benzoyl, 4-methylbenzoyl, 3-methylbenzoyl, 4-cyanobenzoyl, 3-cyanobenzoyl, 4-propylbenzoyl, 2-ethoxybenzoyl, or 4-t-butylbenzoyl; $R_3$, $R_4$ and $R_7$ are each independently $C_1$-$C_3$ alkyl; $R_5$ is methyl or ethyl; and $R_6$ is hydrogen, methyl or methoxy.

Another object of the present invention is to provide a method for preparing the compound at high purity and in high yield.

Technical Solution

In accordance with an aspect of the present invention for achieving the above problem, there is provided a method for preparing 2'-deoxy-2',2'-difluorocytidine represented by Formula I below and a salt thereof, which comprises:

(1) reacting an ethyl 3-hydroxypropionic acid ester of Formula IX with an amine selected from an optically pure (S)-phenylethanamine, (S)-1-(4-methylphenyl)ethanamine, (S)-1-phenyl-1-propanamine, (S)-1-(4-methoxyphenyl) ethanamine and (S)-1-(4-chlorophenyl)ethanamine, to prepare an optically pure 3R-hydroxy propane amide of Formula VIII;

(2) protecting the hydroxyl group of the compound of Formula VIII to prepare a compound of Formula VII;

(3) hydrolyzing the compound of Formula VII to prepare a D-erythro-1-oxoribose of Formula VI;

(4) protecting the 5-hydroxyl group of the D-erythro-1-oxoribose of Formula VI to prepare a D-erythro-1-oxoribose of Formula V;

(5) reducing the D-erythro-1-oxoribose of Formula V to prepare a lactol of Formula IV;

(6) reacting the lactol of Formula IV with methanesulfonyl chloride in the presence of a base such as triethylamine, pyridine or diisopropyl ethylamine to prepare a D-erythro-1-methanesulfonyloxy ribofuranose of Formula III;

(7) glycosylating the D-erythro-1-methanesulfonyloxy ribofuranose of Formula III and a nucleobase, while mixing with an organic solvent such as toluene, 1,2-dichloroethane, anisole or xylene, to obtain a nucleoside of Formula II; and (8) deprotecting the nucleoside of Formula II with a strong base or a strong acid.

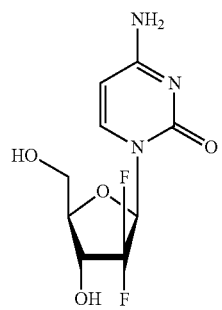

(I)

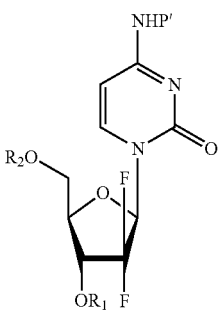

(II)

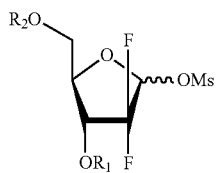

(III)

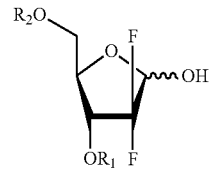

(IV)

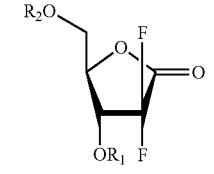

(V)

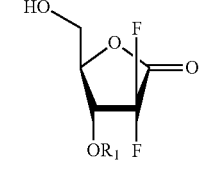

(VI)

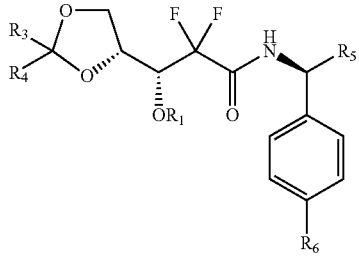

(VII)

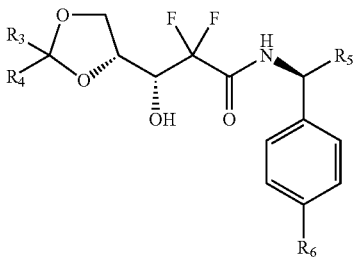

(VIII)

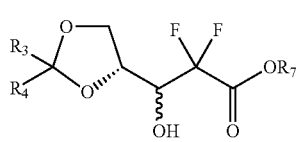

(IX)

wherein $R_1$ and $R_2$ are a protecting group, and when $R_1$ is 1-naphthoyl or 2-naphthoyl, $R_2$ is benzoyl, 4-methylbenzoyl, 3-methylbenzoyl, 4-cyanobenzoyl, 3-cyanobenzoyl, 4-propylbenzoyl, 2-ethoxybenzoyl or 4-t-butylbenzoyl, and when $R_2$ is 1-naphthoyl or 2-naphthoyl, $R_1$ is benzoyl, 4-methylbenzoyl, 3-methylbenzoyl, 4-cyanobenzoyl, 3-cyanobenzoyl, 4-propylbenzoyl, 2-ethoxybenzoyl, or 4-t-butylbenzoyl; $R_3$, $R_4$ and $R_7$ are each independently $C_1$-$C_3$ alkyl; $R_5$ is methyl or ethyl; $R_6$ is hydrogen, methyl or methoxy; $R_7$ is ethyl; and P' is acetyl or hydrogen.

BEST MODE

Hereinafter, the present invention will be illustrated in more detail.

According to the present invention, summaries of the method for preparing the 2'-deoxy-2',2'-difluorocytidine of Formula I and a salt thereof will be given in Reaction Scheme 10 below:

A more-detailed explanation of respective steps of the overall preparation process will be given below. By reacting an ester compound of Formula IX with an optically pure amine in the presence of toluene as a solvent and a sodium cyanide catalyst while refluxing, the compound of Formula VIII, an optically pure 3R-hydroxy amide, can be selectively prepared. The compound of Formula VIII can be readily obtained in a high purity as a solid phase by recrystallization. Since the 3-hydroxyl group of the amide compound of Formula VIII is a reactive functional group, it is first protected to give an amine compound of Formula VII. The protected

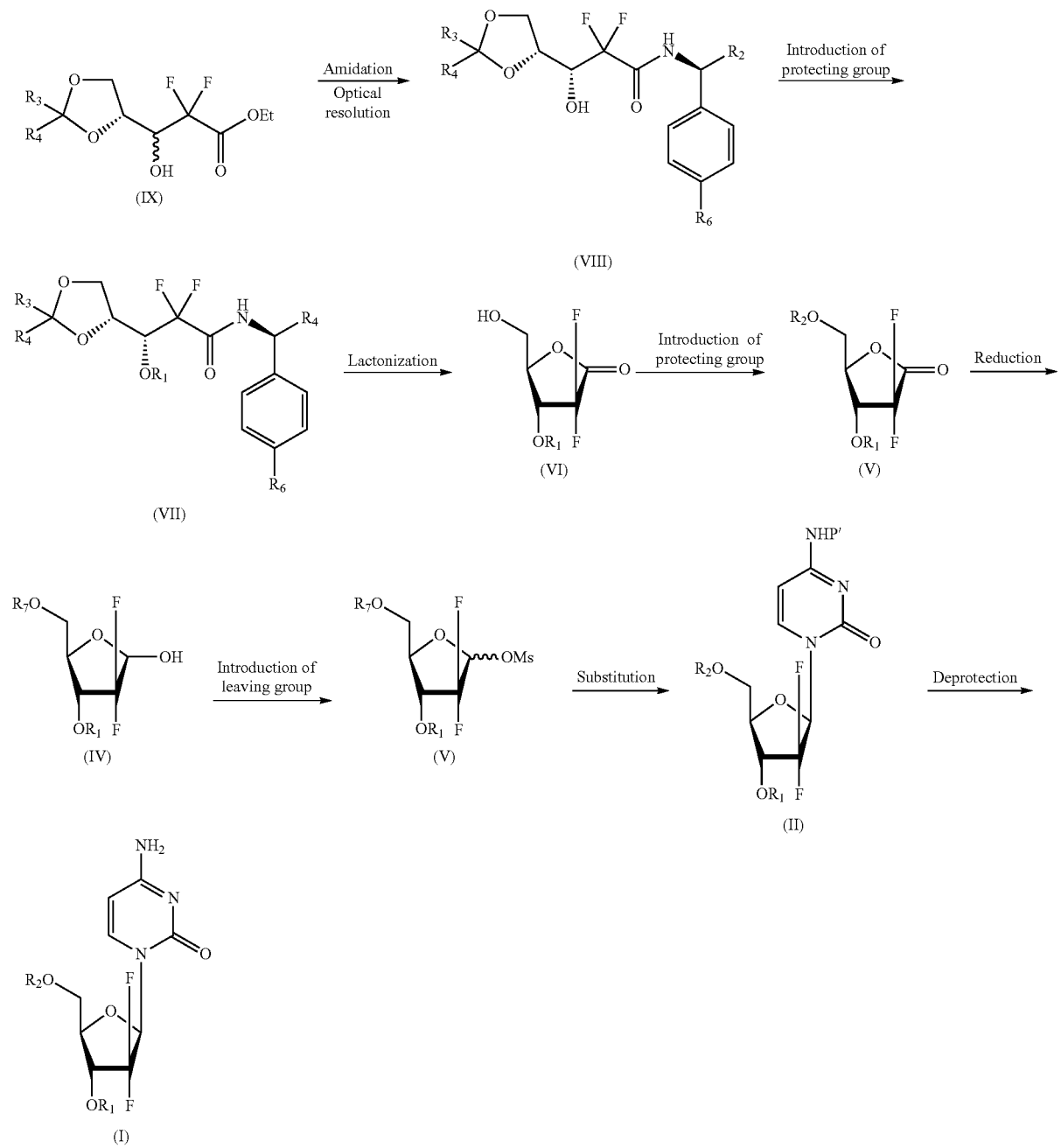

wherein $R_1$, $R_2$, $R_3$, $R_4$, $R_5$, $R_6$ and P' are as defined above.

The compound of Formula IX is an isomeric mixture consisting of a predetermined ratio of 3R- and 3S-enantiomers.

amine compound of Formula VII is reacted with acid to primarily deprotect the dioxolane group. Then, the resulting compound is subjected to lactonization by dehydration at a high temperature to yield an erythro 5-hydroxy-1-oxoribose compound of Formula VI. By protecting the 5-hydroxyl group of the compound of Formula VI in accordance with a conventional method, the erythro-2,2-difluoro-2-deoxy-1-oxoribose compound can be stereoselectively efficiently prepared.

The present invention is advantageous in that the optically pure 3-(2,2-dialkyl-1,3-dioxolan-4-yl)-2,2-difluoro-3-hydroxy)propanamide of Formula VIII can be selectively separated by reacting the enantiomeric mixture of Formula IX with an optically pure amine, as depicted in Reaction Scheme 10. When the enantioselectively pure 3R-3-(2,2-dialkyl-1,3-dioxolan-4-yl)-2,2-difluoro-3-hydroxy)propanamide of Formula VIII thus obtained is used as a precursor, the erythro 1-oxoribose compound of Formula VI can be selectively prepared according to a very simple mechanism.

The compound of Formula VIII is a novel compound, 3R-(2,2-dialkyl-1,3-dioxolan-4-yl)-2,2-difluoro-3-hydroxy) propanamide, which is obtained in a solid phase, not in a liquid phase, can be yielded in a high purity by simple recrystallization, and enables the compounds in a solid phase to be obtained in the subsequent processes, thus avoiding column chromatography and realizing mass-production. In addition, the compound of Formula VIII is useful as an intermediate for medicines, thus broadening applicability thereof.

The (2,2-dialkyl-1,3-dioxolan-4-yl)-2,2-difluoro-3-hydroxy propane ester compound of Formula IX used as a starting material in the method of the present invention can be prepared in accordance with the methods disclosed in U.S. Pat. Nos. 4,965,374, 5,223,608 and 5,434,24. Specifically, as depicted in Reaction Scheme 11 below, an aldehyde ketonide (18) is reacted with a difluoro compound (19) and the mixture is subjected to Reformatsky reaction using zinc to prepare a (2,2-dialkyl-1,3-dioxolan-4-yl)-2,2-difluoro-3-hydroxy propane ester compound of Formula IX (3R-enantiomers:3S-enantiomers=about 3:1).

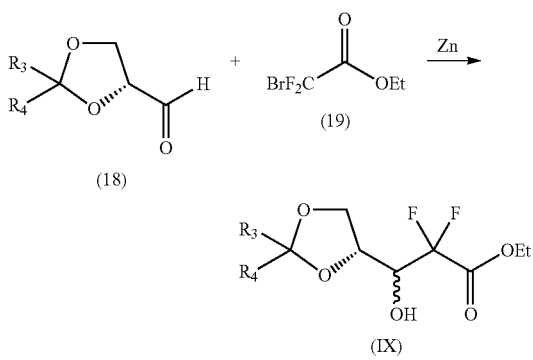

wherein $R_3$ and $R_4$ are as defined above.

Meanwhile, as depicted in the following Reaction Scheme 12, the (2,2-dialkyl-1,3-dioxolan-4-yl)-2,2-difluoro-3-hydroxy propane ester compound of Formula IX (3R-enantiomers:3S-enantiomers=about 3:1) is reacted with an optically pure amine to obtain amide. That is, a 3R-(2,2-dialkyl-1,3-dioxolan-4-yl)-2,2-difluoro-3-hydroxy propane amide compound of Formula VIII can be separated in pure form as a solid.

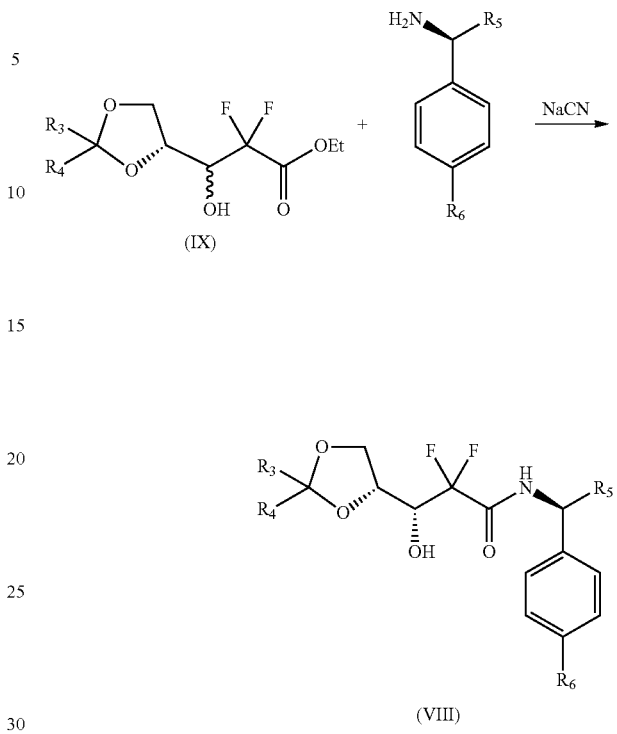

wherein $R_3$, $R_4$, $R_5$ and $R_6$ are as defined above.

By reacting the (2,2-dialkyl-1,3-dioxolan-4-yl)-2,2-difluoro-3-hydroxy propane ester compound of Formula IX as the mixture of 3R- and 3S-enantiomers with optically pure amine, the amide can be optically purely separated. Advantageously, the stereoselectivity of the amide thus prepared can be controlled by properly selecting the amine constituting the amide. Optically active amines that can be used in the present invention include phenyl-containing amines with a structure size and examples thereof include (R) or (S)-phenylethanamine, (R) or (S)-1-(4-methylphenyl)ethanamine, (R) or (S)-1-phenyl-1-propanamine, (R) or (S)-1-(4-methoxyphenyl)ethanamine, (R) or (S)-1-(4-chlorophenyl)ethanamine Of these, preferred are (R) or (S)-phenylethanamine, (R) or (S)-1-(4-methylphenyl)ethanamine, (R) or (S)-1-phenyl-1-propanamine.

Reaction solvents useful for the reaction of Reaction Scheme 12 include single solvents such as toluene, dichloromethane or ethyl acetate in which the compound of Formula IX is highly soluble. Preferably, when using solvents such as toluene or dichloromethane, the compound of Formula VIII is stereoselectively prepared in high yield.

The amide prepared by reacting the (R) or (S) chiral amine with the compound of Formula IX, the enantioselective enantiomeric mixture, can be stereoselectively separated, and is obtained in a solid phase, enabling easy purification. By introducing various protecting groups into the 3-functional hydroxyl groups of the compound of Formula VIII, the compound can be stabilized.

[Reaction Scheme 13]

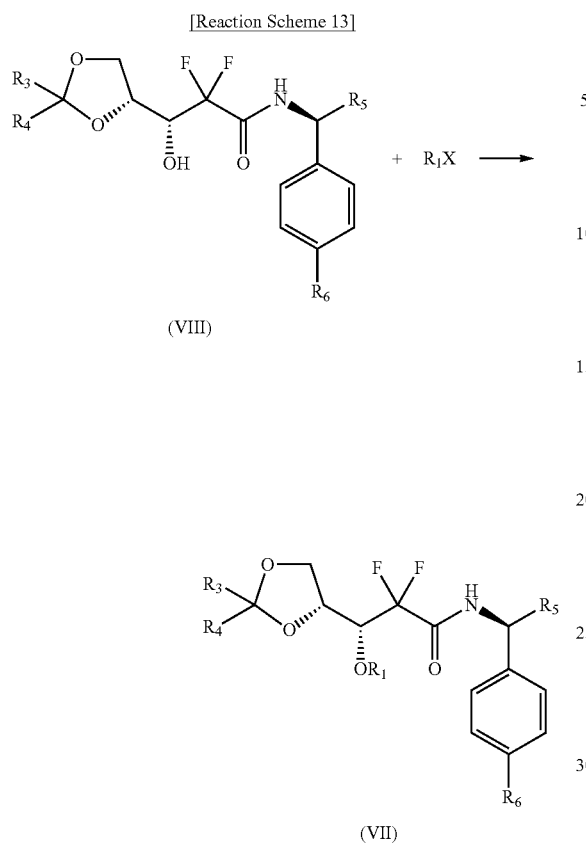

(VIII)

(VII)

wherein $R_1$, $R_3$, $R_4$, $R_5$ and $R_6$ are as defined above.

In the present invention, various protecting groups can be introduced into 3-hydroxyl groups of the compound of Formula VIII. In the case where an acid is produced in the protection process, the acid is neutralized with a base. Examples of useful bases include pyridine, triethylamine, tributylamine, diisopropylethyl amine and methylpiperidine. Of these, triethylamine is the most preferred.

In accordance with the method of the present invention, the amide compound of Formula VIII can be obtained in a high yield of 80% or more, and fNMR spectroscopy results showing one fluorine peak indicate that the amine compound has stereoselectivity of 99% or more. In order to obtain more precise results, the protecting group-introduced compound of Formula V was analyzed using HPLC. From the HPLC analysis, it was confirmed that the compound of Formula V has a very high purity of 99.8% or more (Consequently, 99.6% or more of d.e.), containing reverse isomers in an amount 0.2% or less. These results indicate that it is possible to prepare the compound of Formula VIII with excellent stereoselectivity using the method of the present invention.

Meanwhile, the compound of Formula VI is subjected to lactonization, allowing dehydration under acidic conditions to prepare erythro-2,2-difluoro-2-deoxy-1-oxoribose of Formula VI, the medically-pharmaceutically essential intermediate, as depicted in the following Reaction Scheme 14. By introducing a protecting group into the 5-hydroxyl group of the compound of Formula VI, a more stable compound of Formula V can be prepared.

[Reaction Scheme 14]

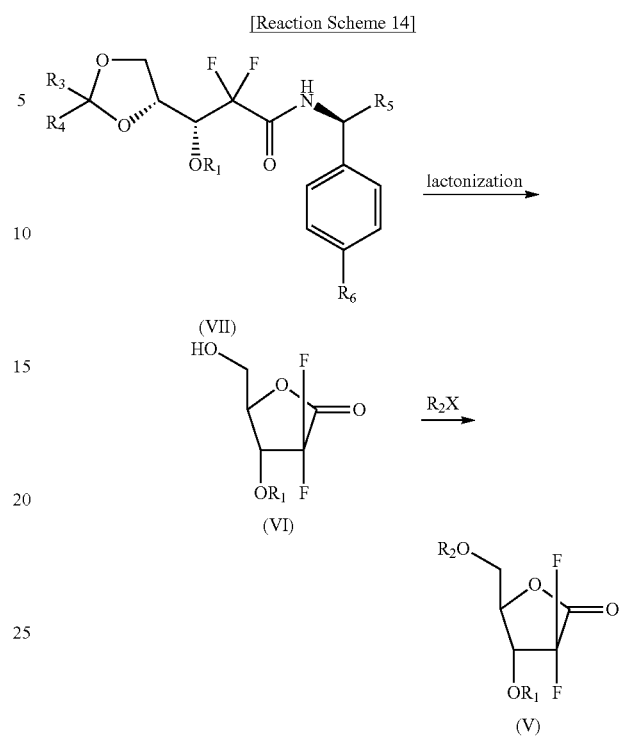

(VII)

(VI)

(V)

wherein $R_1$, $R_2$, $R_3$, $R_4$, $R_5$ and $R_6$ are as defined above.

As the acid used for the lactonization, it is preferable to use a strong acid having a pKa of about −10.0 to about 2.0. Examples of useful acids include inorganic acids such as 1N- to 12N hydrochloric acid, and 1N- to 9N sulfuric acid and organic acids such as methanesulfonic acid, p-toluenesulfonic acid, trifluoroacetic acid and trifluoromethanesulfonic acid. Of these, 12N hydrochloric acid and trifluoroacetic acid are preferred. 12N hydrochloric acid is the most preferred.

The acid may be used in an amount of 2 to 3 mole equivalents, preferably, in an amount of 2.1 to 2.5 mole equivalents, with respect to the compound of Formula VII.

In the process of preparing the D-erythro-2,2-difluoro-2-deoxy-1-oxoribose of Formula V from the D-erythro-5-hydroxy-1-oxoribose compound of Formula VI according to the present invention, the 5-hydroxyl group can be protected using conventional methods, and suitable protecting groups include those containing a hydrophobic benzene or naphthalene ring. Examples of useful protecting groups include benzoyl, phenylbenzoyl, substituted-benzoyl, 1-naphthoyl, 2-naphthoyl, substituted-1-naphthoyl, and substituted-2-naphthoyl, etc. Preferred are benzoyl, 1-naphthoyl and 2-naphthoyl.

In the process of preparing the 5-hydroxy-1-oxoribose compound of Formula VI from the compound of Formula VII and then preparing 2,2-difluoro-2-deoxy-1-oxoribose of Formula V from the compound of Formula VI, the target compound of Formula V may be prepared in a two-step process comprising separating the 5-hydroxy-1-oxoribose compound of Formula VI followed by protection reaction, or in a one-step process (in situ preparation) comprising subjecting the 5-hydroxy-1-oxoribose compound of Formula VI to protection reaction in a single reactor without additional separation of the compound. In comparison with the two-step process, the one-step process of performing the 5-hydroxy protection reaction in a single reactor can avoid yield loss, which occurs in the step of separating the 5-hydroxy-1-oxoribose compound of Formula VI during the two-step process, thus being more advantageous in terms of total yield, enables easy separation of 2,2-difluoro-2-deoxy-1-oxoribose of Formula V in a crystal phase, and can realize a final product purity comparable to that of the two-step process. Accordingly, in practical preparation, the one-step process is more preferable than the two-step process.

Meanwhile, when the erythro 2,2-difluoro-2-deoxy-1-oxoribose of Formula V prepared according to the method of the present invention is analyzed by high performance liquid chromatography (HPLC), the desired erythro 1-oxoribose compound is detected in a very high purity of about 99%, while no threo compound as an isomer is detected.

As such, the method of the present invention enables stereoselective preparation of the D-erythro compound of Formula V in a higher yield through stereoselectivity far superior to conventional methods. Since unique protecting groups can be used to protect each hydroxyl group, physical properties of the compound of Formula V can be controlled via introduction of selective protecting groups. The method of the present invention has other advantages in that the compound of Formula V can be obtained as a solid phase, thus being advantageous in terms of purification and weighing, and can realize an improved yield, thus being advantageous in terms of economic efficiency.

The compound of Formula V enables preparation of novel chiral pools as well as intermediates of gemcitabine as an essential antitumor agent known in the art.

The term "anomer-rich" used in the present invention means a specific anomer present in an excess of one- or more-fold, with respect to opposite anomers, and substantially means an anomeric mixture containing an amount of 98% or more of pure anomers. In addition, the term "anomerization" means a phenomenon in which pure anomers singly or in combination with α- and β-anomers are epimerized in the C-1 position of ribofuranose.

By reducing the D-erythro-1-oxoribose compound of Formula V using conventional methods, the lactol compound of Formula IV can be prepared. Solvents useful for the reduction include non-hydrogenized solvents such as tetrahydrofurane, diethyl ether and dioxane. Useful reducing agents include lithium aluminum hydride, diisobutylaluminum hydride, Red-Al (bis(2-methoxyethoxy)aluminum sodium hydride), lithium tri-tert-butoxyaluminium hydride. Preferred is Red-Al. The reduction is carried out by adding a reducing agent at a temperature of −5 to 0° C. and allowing the reaction to proceed at ambient temperature for 1 to 2 hours. The reduction reaction can be carried out under mild conditions, thus being preferable.

[Reaction Scheme 15]

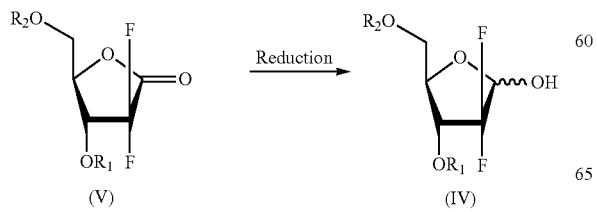

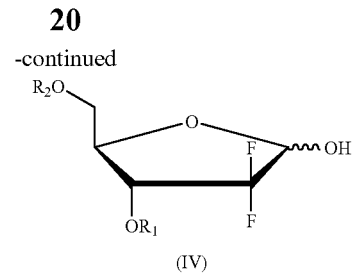

wherein $R_1$ and $R_2$ are as defined above.

The lactol compound of Formula IV is reacted with methanesulfonyl chloride in the presence of a base such as triethylamine, pyridine, or diisopropyl ethylamine to prepare an α-anomer-rich 1-methanesulfonyloxy ribofuranose compound of Formula III. The α-anomer-rich methanesulfonyloxy ribofuranose compound of Formula III is glycosylated with acetylcytosine as the nucleobase to prepare a β-anomer nucleoside of Formula II. Finally, the protecting group of the nucleoside is deprotected with an ammonia/methanol solution to prepare the target 2'-deoxy-2',2'-difluorocytidine of Formula I.

[Reaction Scheme 16]

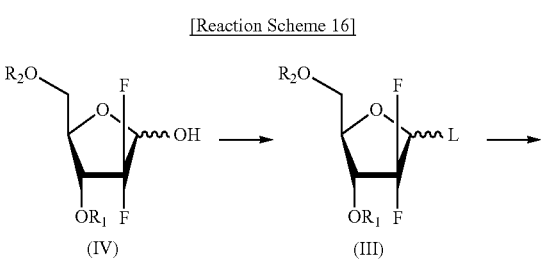

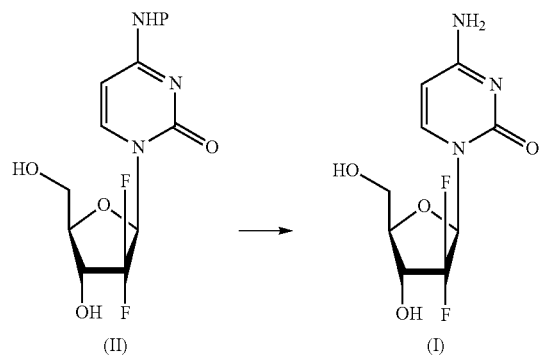

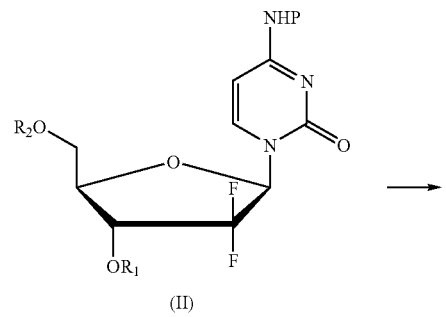

-continued

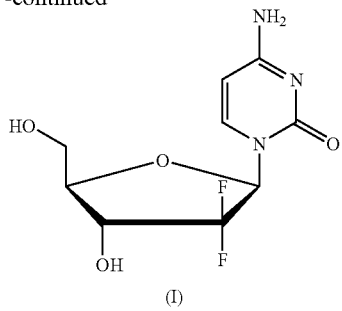

(I)

wherein $R_1$, $R_2$ and P' are as defined above.

Mode for the Invention

The present invention will now be described in further detail with reference to the following examples. These examples are for illustrative purposes only and are not intended to limit the scope of the present invention.

EXAMPLES

Example 1

Synthesis of ethyl 2,2-difluoro-3-hydroxy-3-(2,2-dimethyl-[1,3]dioxolan-4-yl)propionate 13 g (200 mmol) of zinc is added to 26 mL of tetrahydrofurane, 0.1 mL of dibromoethane is added thereto and the resulting mixture is heated at 60° C. for one minute. 0.8 mL (6 mmol) of chloromethylsilane is added to the reaction mixture at 40° C. After 10 minutes, the inner temperature is elevated to 60° C., 25.5 mL (200 mmol) of ethyl bromodifluoroacetate is added to the resulting mixture, and a solution of 30.8 g (237 mmol) 2,2-dimethyl-[1,3]-dioxolane-4-carboaldehyde in 39 mL of tetrahydrofurane is added dropwise thereto and reacted under reflux. After completion of the dropwise addition, the refluxing is continued for 30 minutes. 65 mL of diethylether is added to the reaction solution and the resulting mixture is poured on 260 g of ice. 260 mL of 1N hydrochloric acid is added thereto and then stirred until the ice is completely melted. An aqueous layer is extracted three times with 90 mL of diethylether. An organic layer is collected and sequentially washed with 65 mL of brine and 65 mL of a saturated sodium bicarbonate solution. The organic layer is dried over anhydrous magnesium sulfate and filtered. The resulting residue is distilled under vacuum of 10 Torr to obtain an organic layer separated at 130 to 134° C., thereby yielding the titled compound 1 (8.9 g, yield: 57%, R:S=3:1) as a colorless liquid.

$^1$H NMR (CDCl$_3$, 300 MHz): 3.7~4.4 (m, 6H), 2.90 (d, 1H, (S)—OH), 2.67 (s, 1H, (R)—OH), 1.31-1.52 (m, 9H)

Example 2

Synthesis of 3R-(2,2-dimethyl-1,3-dioxolan-4-yl)-2,2-difluoro-3-hydroxy-N—[(S)-1-phenylethyl]propanamide 150 g (590 mmol) of ethyl 2,2-difluoro-3-hydroxy-3-(2,2-dimethyl-[1,3]dioxolan-4-yl)propionate (R:S=3:1) is dissolved in 750 mL of toluene, a catalytic amount of sodium cyanide is added thereto and 75 mL (590 mmol) of (S)-(−)-α-methylbenzylamine is added dropwise thereto. The reaction solution is refluxed for 24 hours. Ethyl acetate is added to the reaction solution and the resulting mixture is washed three times with 2,000 mL of water. The reaction solution is dried over anhydrous magnesium sulfate, filtered and distilled under reduced pressure to obtain a solid compound. The compound is recrystallized in hexane or a mixed solvent of hexane and ethyl acetate to yield a pale yellow solid (105 g, yield: 54%).

$^1$H NMR (CDCl$_3$, 400 MHz): 7.39-7.28 (m, 5H), 6.66 (m, NH), 5.13 (m, 1H), 4.33-4.24 (m, 2H), 4.05-4.03 (m, 2H), 1.56 (d, 3H, J=6.9), 1.31 (s, 3H), 1.29 (s, 3H)

Example 3

Synthesis of (R)-1-((R)-2,2-dimethyl-1,3-dioxolan-4-yl)-2,2-difluoro-3-oxo-3-((S)-1-phenylethylamine) propyl benzoate 50 g (152 mmol) of the 3R-(2,2-dimethyl-1,3-dioxolan-4-yl)-2,2-difluoro-3-hydroxy-N—[(S)-1-phenylethyl]propanamide obtained in Example 2 is dissolved in 200 mL of methylene chloride, and 32 mL (228 mmol) of triethylamine and 19 mL (167 mmol) of benzoyl chloride are sequentially added to the reaction solution. The resulting mixture is stirred at ambient temperature for 2 hours, and sequentially washed with 600 mL of 1N hydrochloric acid, 600 mL of a 5% saturated sodium bicarbonate solution, and 600 mL of water. The reaction solution is dried over anhydrous magnesium sulfate, filtered and distilled under reduced pressure to obtain a white solid compound. The solid is recrystallized with a hexane-ethyl acetate solution to yield a white solid compound (58.0 g, yield: 88%).

$^1$H NMR (CDCl$_3$, 400 MHz): 8.02 (d, 2H, J=7.2), 7.62-7.59 (m, 1H), 7.47-7.43 (m, 2H), 7.37-7.29 (m, 5H), 6.54 (m, NH), 5.95 (m, 1H), 5.12 (m, 1H), 4.54 (m, 1H), 4.12-4.00 (m, 2H), 1.47 (d, 3H, J=6.9), 1.28 (s, 3H), 1.19 (s, 3H)

Example 4

Synthesis of (R)-1-((R)-2,2-dimethyl-1,3-dioxolan-4-yl)-2,2-difluoro-3-oxo-3-((S)-1-phenylethylamine) propyl 2-naphthoate A white solid compound (63.9 g, yield: 87%) is yielded in the same manner as in Example 3 except that 2-naphthoyl chloride is used instead of the benzoyl chloride.

$^1$H NMR (CDCl$_3$, 400 MHz): 8.62 (s, 1H), 8.03 (dd, 1H, J=1.6, 8.6), 7.95 (d, 1H, J=8.0), 7.91-7.88 (m, 2H), 7.65-7.55 (m, 2H), 7.34-7.26 (m, 5H), 6.58 (m, NH), 6.06-5.98 (m, 1H), 5.15-5.08 (m, 1H), 4.62-4.57 (m, 1H), 4.16-4.08 (m, 2H), 1.46 (d, 3H, J=6.9), 1.29 (s, 3H), 1.19 (s, 3H)

Example 5

Synthesis of 2-deoxy-2,2-difluoro-3-benzoyl-5-(2-naphthoyl)-D-erythro pentofuranos-1-ulose 30 g (68 mmol) of the (R)-1-((R)-2,2-dimethyl-1,3-dioxolan-4-yl)-2,2-difluoro-3-oxo-3-((S)-1-phenylethylamine) propyl benzoate obtained in Example 3 is dissolved in 150 mL of acetonitrile, 14 mL (170 mmol) of a concentrated hydrochloric acid is added thereto and the resulting mixture is refluxed for 4 hours. After completion of the reaction, toluene is added to the reaction mixture, and the solvent and water are distilled and then removed. Toluene is further added to the reaction mixture and then re-distilled to completely concentrate the mixture, thereby obtaining 2-deoxy-2,2-difluoro-D-erythropentofuranos-1-ulose-3-benzoate. The resulting reaction mixture is dissolved in 100 mL of methylene chloride and 8.2 mL (102 mmol) of pyridine is added thereto. A solution of 13 g (68 mmol) of 2-naphthoyl chloride in 40 mL of methylene chloride is added to the reaction solution. The resulting solution is stirred at ambient temperature for 12 hours, and sequentially washed with 200 mL of 1N hydrochloric acid, 200 mL of 5% saturated sodium bicarbonate solution and 200 mL of water. The resulting solution is dried over anhydrous magnesium sulfate, filtered and distilled under reduced pressure. The resulting solid is recrystallized in a hexane-ethyl acetate solution to yield a white solid compound (20 g, yield: 70%).

$^1$H NMR (DMSO-$d_6$, 400 MHz): 8.64 (s, 1H), 8.07 (d, 2H, J=7.2), 8.05 (dd, 1H, J=1.6, 8.6), 7.97 (d, 1H, J=8.0), 7.91-7.89 (m, 2H), 7.66-7.56 (m, 3H), 7.50-7.47 (m, 2H), 5.89-5.78 (m, 1H), 4.60-4.57 (m, 1H), 4.50-4.43 (m, 2H)

Example 6

Synthesis of 2-deoxy-2,2-difluoro-5-benzoyl-3-(2-naphthoyl)-D-erythropentofuranos-1-ulose A white solid compound (20.6 g, yield: 67%) is yielded in the same procedure as in Example 5 except that 2-naphthoyl chloride is used instead of benzoyl chloride.

$^1$H NMR (DMSO-$d_6$, 400 MHz): 8.62 (s, 1H), 8.05 (d, 2H, J=7.2), 8.03 (dd, 1H, J=1.6, 8.6), 7.95 (d, 1H, J=8.0), 7.89-7.87 (m, 2H), 7.65-7.53 (m, 3H), 7.48-7.45 (m, 2H), 6.05-5.95 (m, 1H), 4.62-4.58 (m, 1H), 4.51-4.43 (m, 2H)

Example 7

Synthesis of 2-deoxy-2,2-difluoro-3-benzoyl-5-(2-naphthoyl)-1-methanesulfonyloxy-D-ribofuranose 17.9 g (42 mmol) of the 2-deoxy-2,2-difluoro-3-benzoyl-5-(2-naphthoyl)-D-erythropentofuranos-1-ulose obtained in Example 5 is dissolved in 400 mL of tetrahydrofurane and then cooled to −5 to 0° C. 15.1 mL (50 mmol) of Red-Al (65 wt % in toluene) is slowly added dropwise to the reaction solution and stirred for 5 hours, while maintaining the temperature of −5 to 0° C. 100 mL of 1N hydrochloric acid solution is slowly added dropwise to the reaction solution to complete the reaction. Then, 400 mL of ethyl acetate is added to the reaction solution. An organic layer is washed with 1,000 mL of a 5% saturated sodium bicarbonate solution and 1,000 mL of brine, dried over anhydrous magnesium sulfate, filtered and distilled under reduced pressure to obtain crude 2-deoxy-2,2-difluoro-3-benzoyl-5-(2-naphthoyl)-D-ribofuranose. The crude compound is distilled in 100 mL of methylenechloride and 11.97 mL (88 mmol) of triethylamine is added thereto. 3.99 mL (51 mmol) of methanesulfonyl chloride is added to the reaction solution, the resulting mixture is stirred at ambient temperature for 4 hours, the solvent is removed by vacuum distillation, and 150 mL of ethyl acetate is added thereto. An organic layer is sequentially washed with 400 mL of 1N hydrochloric acid, 400 mL of a 5% saturated sodium bicarbonate solution and 400 mL of brine. The resulting solution is dried over anhydrous magnesium sulfate, filtered, concentrated under reduced pressure to yield a white solid compound (13.6 g, yield: 66%).

$^1$H NMR (CDCl$_3$, 400 MHz): 8.63 (s, 1H), 8.07-8.05 (m, 2H), 7.97-7.89 (m, 3H), 7.66-7.55 (m, 3H), 7.49-7.47 (m, 2H), 5.89-5.76 (m, 1H), 4.60-4.57 (m, 1H), 4.50-4.43 (m, 2H), 4.00 (s, 1H), 3.39 (s, 3H).

Example 8

Synthesis of 2-deoxy-2,2-difluoro-5-benzoyl-3-(2-naphthoyl)-1-methanesulfonyloxy-D-ribofuranose A white solid compound (13.2 g, yield: 64%) is yielded in the same procedure as in Example 7 except that 2-deoxy-2,2-difluoro-5-benzoyl-3-(2-naphthoyl)-D-erythropentofuranos-1-ulose obtained in Example 6 is used instead of the 2-deoxy-2,2-difluoro-3-benzoyl-5-(2-naphthoyl)-D-erythropentofuranos-1-ulose.

$^1$H NMR (CDCl$_3$, 400 MHz): 8.64 (s, 1H), 8.07-8.05 (m, 2H), 7.97 (m, 1H), 7.91-7.89 (m, 2H), 7.67-7.49 (m, 5H), 6.06-5.97 (m, 1H), 4.64-4.59 (m, 1H), 4.54-4.43 (m, 2H), 3.99 (s, 1H), 3.38 (s, 3H)

Example 9

Synthesis of 1-2'-deoxy-2',2'-difluoro-3-benzoyl-5-(2-naphthoyl)-D-ribofuranosyl-4-(1-acetyl)aminopyrimidin-2-one 8.3 g (54 mmol) of acetyl cytosine, 26 mL (126 mmol) of hexamethylsilazane, 1.1 mL (9 mmol) of trimethylsilyl chloride, and 20 mL of toluene are mixed together and refluxed. After being completely dissolved, the mixture is further refluxed for three hours. The reaction solution is allowed to cool to ambient temperature, and then distilled to remove an excess of hexamethylsilazane and trimethylsilyl chloride. After addition of toluene, the reaction solution is re-distilled. 20 mL (108 mmol) of trimethylsilyl trifluoromethane sulfonate is added dropwise to the reaction solution under nitrogen atmosphere, 9 g (18 mmol) of 2-deoxy-2,2-difluoro-3-benzoyl-5-(2-naphthoyl)-1-methanesulfonyloxy-D-ribofuranose obtained in Example 7 is dissolved in 50 mL of toluene, and the resulting solution is added dropwise to the reaction solution, and then refluxed for 15 hours. The reaction solution is allowed to cool to ambient temperature, and 100 mL of ethyl acetate is added thereto. An organic layer is washed with 300 mL of 1N hydrochloric acid, 300 mL of a 5% saturated sodium bicarbonate solution, and 300 mL of brine. The resulting solution is dried over anhydrous magnesium sulfate, filtered, and concentrated under reduced pressure to yield to a white solid compound (8.9 g, yield: 88%).

$^1$H NMR (DMSO-$d_6$, 400 MHz): 8.63 (s, 1H), 8.19-8.15 (m, 1H), 8.07-8.05 (m, 2H), 7.97-7.89 (m, 3H), 7.66-7.55 (m, 3H), 7.49-7.47 (m, 2H), 6.29-6.26 (m, 1H), 5.89-5.76 (m, 1H), 4.60-4.57 (m, 1H), 4.50-4.43 (m, 2H), 4.00 (s, 1H), 2.14 (s, 3H)

Example 10

Synthesis of 1-2'-deoxy-2',2'-difluoro-3-(2-naphthoyl)-5-benzoyl-D-ribofuranosyl-4-(1-acetyl)aminopyrimidin-2-one A white solid compound (8.5 g, yield: 84%) is obtained in the same procedure as in Example 9 except that the 2-deoxy-2,2-difluoro-5-benzoyl-3-(2-naphthoyl)-1-methanesulfonyloxy-D-ribofuranose obtained in Example 8 is used instead of the 2-deoxy-2,2-difluoro-3-benzoyl-5-(2-naphthoyl)-1-methanesulfonyloxy-D-ribofuranose.

$^1$H NMR ((DMSO-$d_6$, 400 MHz): 8.64 (s, 1H), 8.20-8.16 (m, 1H), 8.07-8.05 (m, 2H), 7.97 (m, 1H), 7.91-7.89 (m, 2H), 7.67-7.49 (m, 5H), 6.30-6.26 (m, 1H), 6.06-5.97 (m, 1H), 4.64-4.59 (m, 1H), 4.54-4.43 (m, 2H), 3.99 (s, 1H), 2.12 (s, 3H)

Example 11

Synthesis of 2'-deoxy-2',2'-difluorocytidine hydrochloride 8.5 g (15 mmol) of 1-2'-deoxy-2',2'-difluoro-3-benzoyl-5-(2-naphthoyl)-D-ribofuranosyl-4-(1-acetyl)aminopyrimidin-2-one obtained in Example 9 is added to 85 mL of a 7N-ammonia/methanol solution (Sigma-Aldrich, Inc) and 170 mL of methanol is further added thereto. The mixture is stirred overnight at ambient temperature, distilled under reduced pressure to remove the solvent, 100 mL of water and 70 mL of ethyl acetate are added thereto, an aqueous layer is separated from the mixture, and the ethyl acetate layer is extracted once more with 30 mL of water. The aqueous layer is collected and washed with 40 mL of petroleum ether. 130 mL of IPA is added to the aqueous layer and dissolved while heating. 30 mL of IPA is added to the resulting residue, and then dissolved while heating. 0.92 mL of concentrated hydrochloric acid is added to the reaction solution and then cooled to ambient temperature. The reaction solution is stirred at ambient temperature for 2 hours and the crystals are grown. The resulting precipitated crystals are filtered, washed with a mixed solvent of water and acetone, and dried to yield a white solid compound (2.9 g, 64%).

$^1$H NMR (DMSO-$d_6$, 400 MHz): 10.21 (s, 1H), 9.00 (s, 1H), 8.22 (d, 1H), 6.31 (d, 1H), 6.08 (t, 1H), 4.26-4.17 (m, 1H), 3.95-3.91 (m, 1H), 3.81 (d, 1H), 3.66 (dd, 1H)

Example 12

Synthesis of 2'-deoxy-2',2'-difluorocytidine hydrochloride

A white solid compound (3.0 g, 66%) is yielded in the same procedure as in Example 11 except that 1-2'-deoxy-2',2'-difluoro-3-(2-naphthoyl)-5-benzoyl-D-ribofuranosyl-4-(1-acetyl)aminopyrimidin-2-one obtained in Example 8 is used instead of the 1-2'-deoxy-2',2'-difluoro-3-benzoyl-5-(2-naphthoyl)-D-ribofuranosyl-4-(1-acetyl)aminopyrimidin-2-one.

$^1$H NMR (DMSO-$d_6$, 400 MHz): 10.08 (s, 1H), 8.93 (s, 1H), 8.17 (d, 1H), 6.39 (d, 1H), 6.08 (t, 1H), 4.24-4.18 (m, 1H), 3.93-3.90 (m, 1H), 3.81 (d, 1H), 3.65 (dd, 1H)

Industrial Applicability

As apparent from the above description, the present invention provides a method for preparing gemcitabine, widely used as an antitumor agent to treat various carcinomas including non-small cell lung cancer, pancreatic cancer, bladder cancer, breast cancer and ovarian cancer. In accordance with the method, through reaction with an optically pure amine, an optically pure D-erythro-2,2-difluoro-2-deoxy-1-oxoribose compound can be prepared. Furthermore, gemcitabine can be prepared in a high purity and a high yield using the method of the present invention through the development of intermediates where protecting groups are each independently introduced into the 3- and 5-hydroxyl groups.

The invention claimed is:

1. A method for preparing 2'-deoxy-2',2'-difluorocytidine represented by Formula I and a salt thereof from an optically pure intermediate prepared by optically resolving an ethyl 3-hydroxypropionic acid ester compound as a mixture of R- and S-enantiomers with an optically active amine, which comprises:

(1) reacting an ethyl 3-hydroxypropionic acid ester of Formula IX with an amine selected from an optically pure (S)-1-phenylethanamine, (S)-1-(4-methylphenyl)ethanamine, (S)-1-phenyl-1-propanamine, (S)-1-(4-methoxyphenyl)ethanamine and (S)-1-(4-chlorophenyl)ethanamine, to prepare an optically pure 3-(R)-hydroxy propane amide of Formula VIII;

(2) protecting the hydroxyl group of the compound of Formula VIII to prepare a compound of Formula VII;

(3) hydrolyzing the compound of Formula VII to prepare a D-erythro-1-oxoribose of Formula VI;

(4) protecting the 5-hydroxyl group of the D-erythro-1-oxoribose of Formula VI to prepare a D-erythro-1-oxoribose of Formula V;

(5) reducing the D-erythro-1-oxoribose of Formula V to prepare a lactol of Formula IV;

(6) reacting the lactol of Formula IV with methanesulfonyl chloride in the presence of a base such as triethylamine, pyridine or diisopropyl ethylamine to prepare a D-erythro-1-methanesulfonyloxy ribofuranose of Formula III;

(7) glycosylating the D-erythro-1-methanesulfonyloxy ribofuranose of Formula III and a nucleobase, while mixing with an organic solvent such as toluene, 1,2-dichloroethane, anisole or xylene, to obtain a nucleoside of Formula II; and (8) deprotecting the nucleoside of Formula II with a strong base or a strong acid; wherein the noted Formulas I-IX are identified as follows:

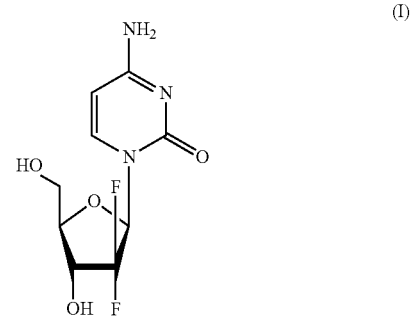

(I)

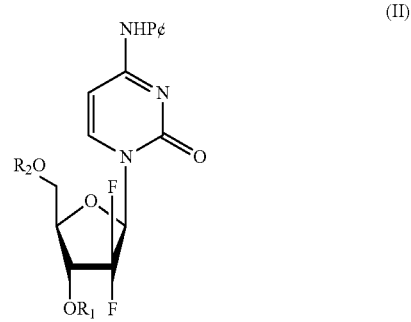

(II)

(III)

-continued

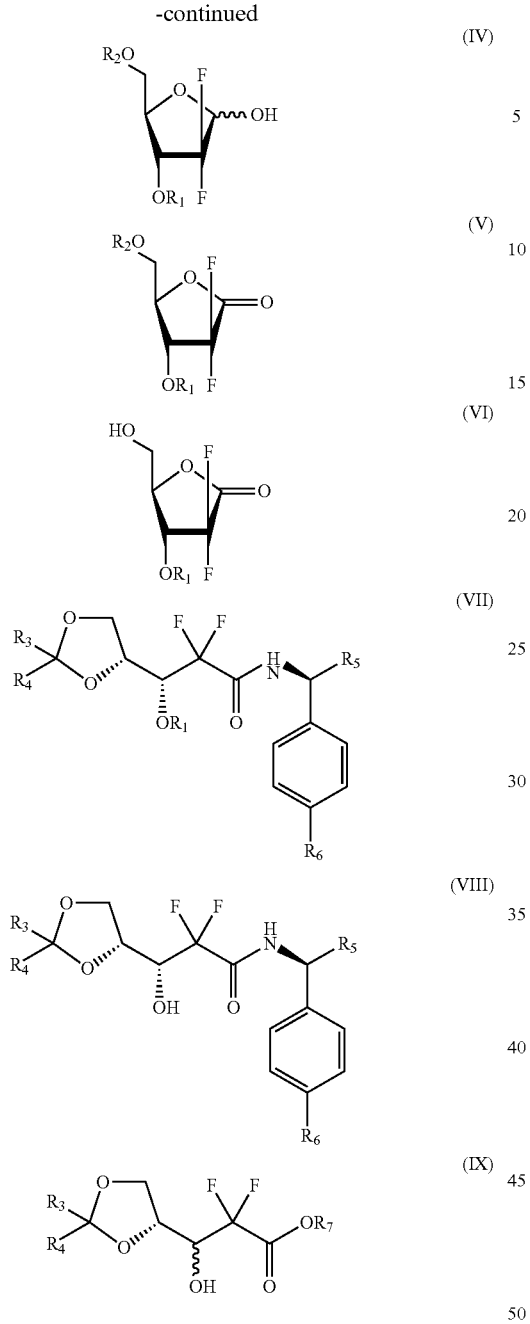

wherein R₁ and R₂ are a protecting group, and when R₁ is 1-naphthoyl or 2-naphthoyl, R₂ is benzoyl, 4-methylbenzoyl, 3-methylbenzoyl, 4-cyanobenzoyl, 3-cyanobenzoyl, 4-propylbenzoyl, 2-ethoxybenzoyl or 4-t-butylbenzoyl, and when R₂ is 1-naphthoyl or 2-naphthoyl, R₁ is benzoyl, 4-methylbenzoyl, 3-methylbenzoyl, 4-cyanobenzoyl, 3-cyanobenzoyl, 4-propylbenzoyl, 2-ethoxybenzoyl, or 4-t-butylbenzoyl; R₃, R₄ and R₇ are each independently $C_1$-$C_3$ alkyl; R₅ is methyl or ethyl; R₆ is hydrogen, methyl or methoxy; R₇ is ethyl; and P' is acetyl or hydrogen.

2. The method according to claim 1, wherein the amine in step (1) is selected from (S)-1-phenylethanamine, (S)-1-(4-methylphenyl)ethanamine and (S)-1-phenyl-1-propanamine.

3. A compound represented by Formula V:

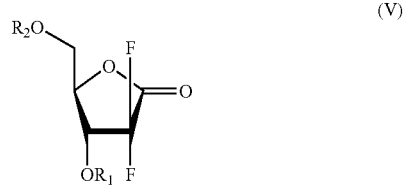

wherein when R₁ is benzoyl, R₂ is 2-naphthoyl; and when R₁ is 2-naphthoyl, R₂ is benzoyl.

4. A compound represented by Formula II:

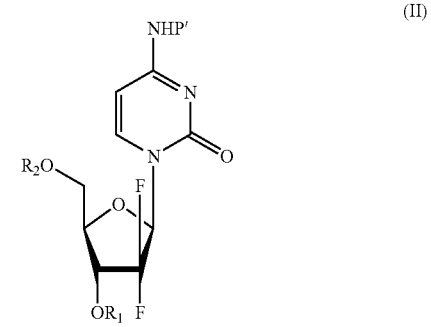

wherein when R₁ is benzoyl, R₂ is 2-naphthoyl; and when R₁ is 2-naphthoyl, R₂ is benzoyl; and P' is an acetyl group or hydrogen.

5. A compound represented by Formula VIII:

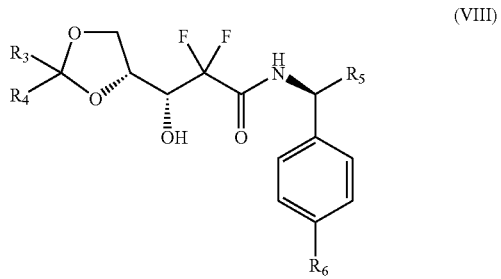

wherein R₃ and R₄ are each independently $C_1$ to $C_3$ alkyl; R₅ is methyl or ethyl; and R₆ is hydrogen, methyl or methoxy.

* * * * *